United States Patent [19]

Mellman et al.

[11] Patent Number: 4,910,131

[45] Date of Patent: Mar. 20, 1990

[54] IDIOTYPE AND ANTI-IDIOTYPE ANTIBODIES USEFUL IN VIRUS DETECTION

[76] Inventors: Ira S. Mellman, 90 Foot Hill Rd., North Ford, Conn.; David Vaux, 65 Lawrence St., New Haven, Conn.; Ari H. Helenius, 465 Whitford St., Gilford, Conn.

[21] Appl. No.: 137,237

[22] Filed: Dec. 23, 1987

[51] Int. Cl.[4] ........................ C12Q 1/70; C12N 15/00; G01N 33/53

[52] U.S. Cl. ........................................ 435/5; 435/7; 435/172.2; 435/235; 435/948; 436/548; 530/387; 530/808; 530/809; 530/826

[58] Field of Search .................... 435/5, 7, 192.2, 235, 435/948; 436/548, 63; 530/387, 808, 809, 826

[56] References Cited

U.S. PATENT DOCUMENTS 4,699,880 10/1987 Goldstein ........................ 435/172.2

OTHER PUBLICATIONS

Vaux et al., *Nature*, vol. 336(3), pp. 36–42, (Nov. 1988).
Vaux et al., *J. Cell. Biology*, vol. 105, p. 589, (1987).
Kennedy et al., *Scientific American*, vol. 255(1), pp. 40–48, (1986).
Norton et al., *Cellular Immunology*, vol. 109, pp. 419–428, (1987).
*Microbiology*, (2nd Ed.), Davis et al., Harper & Row, Hagerstown, Md., pp. 1314, 1324, (1973).
Kohler et al., *Nature*, vol. 256, pp. 495–497, (Aug. 7, 1975).
Gaulton, et al., "INDIOTYPIC MIMICRY OF BIOLOGICAL RECEPTORS", *Ann. Rev. Immunol.*, 4, 1986, pp. 253–280.
Borrebaeck & Moeller, "IN VITRO . . . AND WEAK INNUNOGENS", *J. of Immunol.*, 1986, pp. 3710–3715.
Mellman, "SELECTIVE IODINATION . . . PINOCYTIC VESICLES", *J. of Cell Biol.*, 86, 1980, 712–722.
Reading, "THEORY AND . . . ANTIBODY PRODUCTION", *J. of Immunol. Methods*, 53, 1982, pp. 261–291.

Davie, et al., "STRUCTURE CORRELATES OF IDIOTYPES", *Ann. Rev. Immunol.*, 4, 1986, pp. 147-165.

Abood, "CHARACTERIZATION OF . . . ANTI—IDIOTYPIC ANTIBODIES", *Proc. Natl. Acad. Sci. USA*, 84, 1987, 6587-6590.

Kubagawa, et al., "ANALYSIS OF . . . ANTI—IDIOTYPE ANTIBODIES", *J. of Immunol.*, 1987, pp. 435–439.
Schreier & Lefkovits, "INDUCTION OF . . . SPLEEN CELLS", *Immunol.*, 36, 1979, pp. 743–752.
Luben, "IN VITRO . . . ACTIVATING FACTOR", *Molecular Immunology*, 17, 1980, pp. 635–539.

(List continued on next page.)

*Primary Examiner*—Robert J. Warden
*Assistant Examiner*—Janelle Graeter
*Attorney, Agent, or Firm*—Merchant, Gould, Smith, Edell, Welter & Schmidt

[57] ABSTRACT

The invention describes a new process for the production of anti-viral diagnostics, as well as an example of one antibody useful in detecting a wide variety of pathogenically important alphaviruses. The process includes, but is not limited to, the isolation of monoclonal antibodies directed against internal viral components. Such antibodies may be generated by conventional immunization in vivo or in vitro using subviral particles or synthetic peptides corresponding to specific viral proteins. Alternatively, synthetic peptides derived from the cytoplasmic domains of envelope proteins may be used to elicit monoclonal idiotypic and anti-idiotypic antibodies following immunization in vitro and/or in vivo.

The anti-alphavirus antibody included in the invention is an example of the type of reagent produced. It was produced as an anti-idiotype against monoclonal antibodies to a synthetic peptide derived from Semliki Forest virus. The monoclonal anti-idiotype is specific for the genome-containing nucleocapsid structure not only of Semliki Forest virus, but of every alphavirus tested thus far.

21 Claims, 5 Drawing Sheets

OTHER PUBLICATIONS

Luben, "MONOCOLNAL ANTIBODIES . . . OF ANTIGEN", *Science,* 218, 1982, pp. 887-889.

Pain et al., "IDENTIFICATION OF . . . CONTACT ZONES", *Nature,* 331, 1988, pp. 232-237.

Rathjen and Underwood, "OPUMIZATION OF . . . PEPTIDE HORMONES", *J. of Immunol. Methods,* 78, 1985, pp. 227-237.

Sege, et al., "USE ANTI—IDTIOTYPIC . . . RECEPTOR PROBES", *Proc. Natl. Acad. Sci.,* 75, 1978, pp. 2443-2447.

Van Ness, "IMMUNIZATION IN VITRO . . . IMMUNOGENIC PROTEINS", *Proc. Natl. Acad. Sci.,* 81, 1984, pp. 7897-7901.

Helenius, "THE EFFECTS OF . . . VIRUS MEMBRANE", *Eur. J. Biochem.,* 106, 1980, pp. 613-618.

Fuller & Argos, "IS SANDBIS A SIMPLE PICORNAVIRUS WITH AN ENVELOPE?", *The EMBO Journal,* 6, 1987, pp. 1099-1105.

Erlanger, et al., "AUTO—ANTI—IDIOTYPE: A BASIS FOR . . . ANTI—RECEPTOR ANTIBODIES", *Immunol. Review,* 1986, pp. 23-37.

Co, "ISOLATION AND . . . CELL—SURFACE RECEPTOR", *Proc. Natl. Acad. Sci.,* 82, 1985, pp. 1494-1498.

Co, et al., "STRUCTURAL SIMILARITIES . . . TYPE 3 RECEPTORS", *Proc. Natl. Acad. Sci.,* 82, 1985, pp. 5315-5318.

Knigg, et al., "IMMUNOCYTOCHEMISTRY OF . . . ANTI—IDIOTYPIC ANTIBODY", *Cell Tissue Res.,* 246, 1986, pp. 509-513.

Elias, "ANTIBODIES TO . . . WITH HYPOGLYCEMIA", *Diabetes,* 36, 1987, pp. 348-354.

Farid, et al., "ANTIIDIOTYPIC ANTIBODIES . . . STRUCTURE AND FUNCTION", *Endocrine Reviews,* 6, 1985, pp. 1-23.

Garoff, "LOCATION OF THE . . . FOREST VIRUS MEMBRANE", *Proc. Natl. Acad. Sci.,* 71, 1974, pp. 3988-3992.

Simons & Warren, "SEMLIKI FOREST VIRUS: A PROBE . . . IN THE ANIMAL CELL", *Adv. In Protein Chem.,* 36, 1984, pp. 79-132.

Dalgarno, et al., "ROSS RIVER VIRUS . . . ENCODED STRUCTURAL PROTEINS", *Virology,* 129, 1983, 170-187.

Chamberlain, "FLUROGRAPHIC DETECTION . . . SODIUM SALICYLATE", *Anal. Biochem.,* 98, 1979, 132-135.

Fuller, "THE T=4 ENVELOPE . . . COMPLEMENTARY T=3 CAPSID", Cell 48, 1978, 923-934.

Laemmli, "CLEAVAGE OF STRUCTURAL . . . BACTERIOPHAGE T4", *Nature,* 227, 1970, pp. 680-685.

Scheele and Pfefferkorn, "KINETICS OF . . . SANDBIS VIRUS", *J. Virol., 3, 1969, pp. 369-375.*

Simons & Garoff, "THE BUDDING MECHANISMS OF ENVELOPED ANIMAL VIRUSES", *J. gen. Virol.,* 50, 1980, 1-21.

Wengler, et al., "THE CORE PROTEIN . . . NUCLEIC ACIDS IN VITRO", *Virology,* 118, 1982, pp. 401-410.

Wassermann, "ANTI—IDIOTYPIC ROUTE . . . MYASTHENIA GRAVIS", *Proc. Natl. Acad. Sci. USA,* 79, 1982, 4810-4814.

Bradford, "A RAPID AND . . . PROTEIN—DYE BINDING", *Anal. Biochem.,* 1976, pp. 248-254.

IDIOTYPE AND ANTI-IDIOTYPE ANTIBODIES USEFUL IN VIRUS DETECTION

This invention was made with the assistance of Grant Nos. GM-29765, GM-33904, and AI-18599 from the National Institute of Health. The Government has certain rights in the invention.

TECHNICAL FIELD

The present invention relates to idiotype and anti-idiotype antibodies useful in virus detection and a process to isolate monoclonal antibodies directed against internal viral components, such as the nucleocapsid structures.

BACKGROUND OF THE INVENTION

Most monoclonal antibodies and antisera to human and animal viruses are derived from conventional in vivo immunization using whole virus, isolated envelope protein components, or synthetic peptides derived from proteins exposed on the virus exterior. Thus, these reagents are uniformly directed against external viral components. The usefulness of such antibodies for diagnostic purposes is limited by the poor cross reactivity among even closely related viruses, a consequence of the extensive genetic drift affecting the amino acid sequences of externally oriented viral proteins. Due to this poor cross reactivity these anti-viral antibodies are not useful for routine screening and diagnoses—antibodies produced against one isolate of a genetically variable virus (such as HIV or influenza) will often fail to react with the virus infecting a second set of patients. Also, typical diagnostic tests which detect viral infections measure the level of circulating anti-viral antibodies in a patient's serum and do not directly measure the presence of the virus. Therefore, a need exists for a method to directly identify related but serologically distinct viruses.

SUMMARY OF THE INVENTION

We have developed a method which permits the production of a new generation of monoclonal antibodies which should have wide application as highly sensitive, reproducible, and cross-reactive viral diagnostic and screening reagents. The antibodies, which represent a unique class of "anti-virus anti-idiotypes", are simple to use and should be readily adaptable to kit form. The method has been demonstrated for an important class of viruses responsible for causing a variety of encephalitis syndromes, but should be equally efficacious for virtually any class of enveloped virus, including: HIV (AIDS virus), other tumor-causing retroviruses, influenza virus, rhabodviruses, and the herpes viruses.

Unlike most conventional diagnostics which detect viral infections by measuring the level of circulating anti-viral antibodies in a patient's serum, the present invention makes possible new antibody reagents which directly measure the presence of a virus in any suitable patient sample. The key to these antibody reagents is that they are produced against highly conserved functional domains of the virus. In accordance with the invention highly conserved internal viral components are targeted for antibody production, by the use of synthetic peptides to internal components, by the production of anti-idiotype antibodies, and by the generation of antibodies by immunization in vitro. Thus, the present invention provides anti-idiotype antibodies for detecting any strain or serotype within a group of related viruses with similar efficiency.

For example, the monoclonal anti-idiotype described herein is unique in its specificity and in its ability to cross react with a variety of related alphaviruses. The anti-alphavirus antibody will have immediate use as a sensitive diagnostic tool for the presence of diverse viral subtypes in patient samples using a simple ELISA assay. These tests should be easily adaptable to kit form. The process used to generate this antibody can now and in the future be used to generate other similar such reagents specific for virtually any enveloped virus, including but not limited to HIV (the causative virus of AIDS), HTLV-I, influenza virus, oncogenic retroviruses, herpes virus, etc.

Reagents made in accordance with the present invention can be produced in the laboratory without any necessity for large scale propagation of the virus of interest, eliminating the need for establishing expensive and potentially biohazardous systems for virus propagation or cDNA expression. Use of anti-idiotype antibodies according to the present invention, for detection of viruses provides a number of major advantages over conventional virus diagnostics. These advantages include: (1) high degree of cross reactivity among related but serologically and genetically distinct viruses, thus, (a) a single reagent should be applicable for screening and detection in patients infected by otherwise highly variable virus types; and (b) there is no need to have isolated or even identified the precise strain of virus thought to have infected a particular patient or population (2) ease, safety, and low cost of production; (3) detection of virus in any suitable patient sample, including physiological fluids such as serum or plasma and tissue samples; (4) detection does not rely on a patient's antibody response to a viral infection; (5) easy adaption to kit form in conjunction with colorimetric ELISA assay; (6) potential applicability to any enveloped virus type (HIV, influenza, etc.) as demonstrated for an important class of encephalitic viruses.

BRIEF DESCRIPTION OF THE FIGURES

FIG. 1 shows the specificity of a polyclonal antibody response to the SFV peptide. The synthetic SFV peptide ("SP62 Ag.") and an irrelevant synthetic peptide (SP76 AG.") were immobilized on plastic (96 well microtiter wells [manufactured by Nunc]) and the reactivity of the antibody against each was tested by ELISA assay. No reactivity above background was observed against the irrelevant peptide.

FIG. 3 shows the distribution of F13.3C5 antigen by indirect immunofluorescence microscopy. BHK-21 cells were plated on glass slides and infected (panel A) or mock-infected (panel B) with SFV. After 5 hr, the cells were fixed, permeabilized, and processed for immunofluorescence using a rabbit anti-SFV spike antiserum as the first antibody. Also shown are the reactivity of F13.3C5 IgM on infected (panel C) and mock-infected (panel D) cells, and the reactivity of an authentic rabbit anti-SFV capsid antibody on infected (panel E) and mock-infected (panel F) cells.

FIG. 5 shows the quantitative determination of the results illustrated in FIG. 4. Individual radioactive bands were excised from the SDS-polyacrylamide gel and radioactivity determined by liquid scintillation spectrometry.

DETAILED DESCRIPTION OF THE INVENTION

The present invention utilizes the structural mimicry of antigens by a subclass of anti-idiotype antibodies ("internal image anti-idiotypes", see Gaulton and Greene, *Am. Rev. Immunol.*, 4:253–80, 1986). Detection of viruses in accordance with the present invention is demonstrated herein by producing an anti-idiotype antibody capable of identifying alphaviruses. It will be understood, however, that the present invention can be used to produce anti-idiotype antibodies useful to detect any enveloped virus including but not limited to HIV, HTLV-1, influenza virus, oncogenic retroviruses, herpes virus and the like.

Alphaviruses are simple enveloped single stranded RNA viruses which consist of a lipid bilayer membrane ("envelope") surrounding an RNA-protein core ("nucleocapsid"). Virus particles consist of only three or four structural proteins each of which is encoded by the viral RNA genome. Newly formed virus escapes from infected host cells by a budding step through the host cell plasma membrane. Although the viral envelope is thus derived from the host cell membrane, the budding process is so specific that each new virus contains exactly 240 copies of the viral spike glycoproteins (those membrane-bound proteins characteristic of the virus surface) without any contamination of host cell membrane proteins. This high degree of specificity is the likely result of specific interactions between intracellular nucleocapsids and the cytoplasmic domains of the spike glycoproteins. By binding to the cytoplasmic domains of the spike glycoproteins, the nucleocapsids ensure that only virally-encoded membrane proteins—and not endogenous host cell proteins presumably unable to specifically bind the nucleocapsids—are included in the nascent virion. This general mechanism we believe applies to the biogenesis of all classes of enveloped viruses, and it has been best characterized for one well studied alphavirus, Semliki Forest virus (SFV).

We produced monoclonal antibodies against those epitopes involved in the interaction of Semliki Forest Virus (SFV) spike glycoproteins with nucleocapsid. First, a polyclonal response was generated in vitro against a synthetic peptide corresponding to the cytoplasmic domain of the E2 spike glycoprotein to provide a library of anti-peptide idiotypes. It is to be understood that these anti-peptide idiotypes can be useful for virus detection by one of skill in its art based on the specificity of the antibody to the highly conserved SFV E2 cytoplasmic domain.

Using these anti-peptide antibodies, we next performed a second in vitro immunization and selected monoclonal anti-idiotype reagents with viral specific reactivity. These antibodies were shown to recognize an epitope on the SFV nucleocapsid protein. To confirm that this anticapsid reactivity represents an authentic anti-idiotypic response to the original antipeptide antibodies, we also generated anti-idiotype antibodies against the anti-capsid reagents. These antibodies are now anti- anti-idiotypes and were specifically reactive with the cytoplasmic domain of glycoprotein E2. This reconstitution of three consecutive steps of an idiotypic network confirms the existence of a specific interaction between the SFV capsid protein and the spike glycoprotein cytoplasmic domain and provides a method to verify the desired specificity of the idiotype antibody for use as a diagnostic reagent.

REAGENTS AND MATERIALS

Reagents

Fetal calf serum was obtained from J.R. Scientific, Woodland, Calif. Type 100 Rabbit serum was obtained from Diagnostic Biochemicals Inc., San Diego, Calif. Alpha-MEM was prepared from powdered stock obtained from Flow Laboratories. Nutridoma-SP defined serum substitute was from Boehringer Mannheim. Fluorescein, rhodamine or alkaline phosphatase conjugated affinity purified Goat anti-mouse IgG, Goat anti-mouse IgM and Goat anti-rabbit second antibodies were obtained from Zymed Inc., San Francisco, Calif. $^{35}$S-methionine was obtained from ICN. All other materials were of reagent grade and were obtained from Sigma Co., St. Louis, Mo.

Antibodies

Rabbit polyclonal antisera against isolated SFV capsid or against the 29S complex containing viral spike glycoproteins was produced and is available from Dr. I.

Mellman at Yale University School of Medicine. The antisera is produced by immunizing rabbits with isolated SFV capsid or 29S complex containing viral spike glycoproteins in accordance with procedures well known to those skilled in the art.

Animals

Balb/c and C57/B1 female mice were obtained from Jackson Laboratories (Bar Harbor, Me.) and used at three weeks of age for isolation of thymocytes and twelve weeks of age for in vitro and in vivo immunizations.

Media and Cell lines

The myeloma parent used was SP-2 obtained from the American Type Culture Collection, (ATCC No. CRL-1581). Myeloma and hybridoma lines were grown in Normal Lymphocyte Medium (NLM) consisting of alpha-MEM supplemented with 2 mM sodium pyruvate, 50 $\mu$M 2-mercaptoethanol, 1x Gibco non-essential amino acids, 10 mM HEPES pH 7.2 and 20% heat inactivated fetal calf serum. Baby hamster kidney (BHK-21) cells (available from ATCC, No. CC1-21) were grown in monolayer culture in Dulbecco's MEM supplemented with 5% heat inactivated fetal calf serum.

Preparation Methods of Synthetic Peptides

Peptides were synthesized on an Applied Biosystems (Foster City, Calif.) 430A peptide synthesiser, cleaved with HF, and purified by preparative HPLC on a Waters Delta Prep system. Peptide identity was confirmed by amino acids analysis.

Preparation of Thymic MLR Supernatants

Single cell suspensions from the thymuses of three week old Balb/c and C57/B1 mice were co-cultured at a density of $2 \times 10^6$ thymocytes of each strain per ml. in a medium consisting of alpha-MEM with 50 $\mu$M 2-mercaptoethanol and 2% type 100 rabbit serum. After 48 hours, the supernatant was collected, clarified by centrifugation and 0.22 $\mu$m filtered prior to storage at $-20°$ C. The supernatant retained the ability to support in vitro immunization for at least six months when prepared in this way.

In Vitro Immunization

In vitro immunizations were performed by a modification of the method of Borrebaeck and Moller, *J. Immunol.*, 136:3710-3715 (1986). For each immunization, spleens were dissected from two twelve week old Balb/c mice and a single cell suspension was prepared by teasing the organs apart with two 18 G needles. The cells were washed twice in alpha-MEM containing 50 $\mu$M 2-mercaptoethanol and resuspended to a final volume of 30 ml. in a medium consisting of 50% NLM and 50% thymic conditioned medium. The cell density was approximately $1 \times 10^7$ nucleated cells per ml. 10-20 $\mu$g. antigen (sterilized by 0.22 M filtration) in a volume of 0.1 to 1.0 ml. was then added and the mixture cultured in a T75 flask at 37° C., in 5% $CO_2$ without disturbance for five days. At the end of this time the non-adherent cells were released by brisk shaking and harvested by centrifugation at $400 \times G$ for 5 minutes. The supernatant was retained for analysis of secreted immunoglobulin and the cells were used for hybridoma production by fusion with SP-2 myeloma cells (see below). The supernatant was concentrated fifteen fold by dialysis (using dialysis tubing) against solid poly-ethylene glycol of mean $M_r$ 20,000 and tested for the presence of antigen specific immunoglobulin by indirect immunofluorescence or ELISA.

Production of Monoclonal Antibodies

Spleen cells immunised either in vivo or in vitro were fused to the SP-2 myeloma line using polyethylene glycol as described by Mellman, et al., *J. Cell Biol.*, 86:712-722, (1980). Feeder layers consisting of total syngeneic mouse peritoneal exudate cells at $1 \times 10^5$ per well in 0.3 ml NLM were established in 24 well plates 24 hr. before use. The fusion mixture was plated at $1 \times 10^5$ spleen input cells/well in 0.3 ml NLM containing 100 $\mu$M (1 $\times$) hypoxanthine and 2 $\mu$g/ml (1 $\times$) azaserine. After 24 hours the wells were fed with 0.3 ml NLM containing 2x hypoxanthine and 2x azaserine. Subsequently wells were fed by exchange with 0.5 ml NLM containing only 1x hypoxanthine on alternate days until ready for screening, which was usually on days 8-12. Fusion well supernatants were screened either by ELISA using peptide as the solid phase antigen or by indirect immunofluorescence on fixed, permeabilized cells (see below). Positive wells were cloned at least twice in soft agar over peritoneal exudate feeder cells. Stably cloned hybridomas secreting antibodies of interest were transferred by gradual dilution into serum free Nutridoma (Boehringer Ingelheim Ltd.) medium (according to manufacturer's instructions) to facilitate isolation of immunoglobulin. Immunoglobulin was isolated from Nutridoma supernatant by precipitation with ammonium sulfate at 70% saturation (24 hr at 4° C.).

ELISA Assays

Solid phase substrates were prepared by drying 5 $\mu$g/well of each peptide from a solution in distilled water onto wells of Nunc Immunolon 96 well plates overnight at 42° C. Other substrates were plated at 50 $\mu$l/well or 100 $\mu$g/ml protein in 0.1 M sodium carbonate buffer at pH 8.5 and incubated overnight at 4° C. Non-specific sites were blocked by preincubation with 100 $\mu$l/well calcium and magnesium free phosphate buffered saline, (PBS, available from Gibro Laboratories) (CMF.PBS) containing 10% normal goat serum for 2 hours at room temperature. Wells were then washed briefly with CMF.PBS and incubated with 50 $\mu$l/well of the test supernatants for 2 hours at room temperature. The plates were washed in five changes at CMF.PBS over 30 minutes and then reblocked with CMF.PBS containing 10% goat serum for 30 minutes. Appropriate alkaline phosphatase conjugated goat second antibodies were then added at 50 $\mu$l/well at dilutions from 1:300 to 1:800 in CMF.PBS containing 10% goat serum. After two hours the plates were washed as before and then incubated with a commercial phosphatase substrate (disodium p-nitrophenyl phosphate, Sigma 104-105) in 50 mM sodium glycinate pH 8.7 containing 4 mM magnesium chloride at room temperature. Plates were read in an automatic plate scanner. Readings were taken hourly until the positive control went off scale (>30.0 units, usually three hours)—at this time any well more than 5 times above background was scored as positive.

Indirect Immunofluorescence Assays

BHK cells were plated at 80% confluence on multiwell slides (Carlsson Scientific Co.) and infected at a multiplicity of infection (MOI) between 10 and 100 with SFV or other alphaviruses in RPMI supplemented with 1 mg/ml BSA and 10 mM HEPES pH 6.8 for a continuous five hours. Alphaviruses other than SFV (and flaviviruses) were kindly provided by Dr. R. Shope, Arbovirus Research Unit, Department of Epidemiology and Public Health, Yale University School of Medicine and were handled exclusively in their facility under appropriate containment protocols. Mock infected cells were incubated in the same buffer without virus. The cells were washed twice with CMF.PBS and fixed with methanol for 6 minutes at −20° C. Nonspecific sites were blocked with CMF.PBS containing 10% goat serum for 30 minutes and the wells were incubated with candidate monoclonal antibody supernatant (15 µl) for one hour. For double label immunofluorescence both first antibodies were applied together (25 µg/ml purified mouse IgM for the monoclonal F13.3C5 and empirically determined dilutions for the rabbit polyclonal antisera). The slides were washed five times in CMF.PBS and incubated in CMF.PBS containing 10% goat serum for 30 minutes. Fluorochrome conjugated second antibody diluted 1:40 (appx. 5 µg/ml) in CMF.PBS with 10% goat serum (or a mixture of two second antibodies for double label immunofluorescence) was then applied to the slides and incubated for one hour. After washing in CMF.PBS and water the slides were mounted in plastic resin (Moviol, Calbiochem-Behring, LaJolla, Calif.) and examined with a Zeiss Photomicroscope III equipped with epifluorescent illumination. Results were photographed using Kodak Tri X Pan film rated at 800 ASA or Ektrachrome 400ASA with exposures ranging from 30 seconds to 3 minutes.

(Preparation of Radiolabelled Homogenates of SFV Infected BHK-21 Cells

BHK-21 cells were plated to 70% confluence in 100 mm tissue culture dishes and infected the following day with SFV at an MOI of 500 in 5 ml/dish of an RPMI buffer containing 1 mg/ml BSA and 10 mM HEPES pH 6.8. After 120 minutes at 37° C. the plates were washed twice in the RPMI buffer and incubated for 30 minutes at 37° C. in methionine-free medium containing 2 µg/ml Actinomycin D. This medium was then aspirated and replaced with 5 ml of the same medium containing 0.5 mCi$^{35}$S methionine. The plates were then incubated at 37° C. for 150 minutes, washed three times in PBS and harvested by scraping in 4 ml/dish of cold homogenization buffer, consisting of PBS supplemented to 300 mM sodium chloride, 2 mM EDTA, 20 mM sodium azide, 1 mM phenyl-methyl-sulfonylchloride, 0.22 U/ml aprotinin and 200 µg/ml BSA at a final pH of 8.2. The cells were homogenized by 8 strokes of a tight fitting precooled stainless steel Dounce homogenizer and centrifuged in a Beckman microfuge at 4° C. for 5 minutes. This post nuclear supernatant was stored at −70° C. until used.

Immunoprecipitation from Homogenates

Radiolabelled homogenates of SFV infected BHK cells were prepared as above and incubated in aliquots of 50 µl with 10 µg of purified mouse monoclonal antibodies (F13.3C5 or other mouse monoclonal antibodies). All incubations were performed at 4° C. on an Eppendorf microshaker. After two hours to allow antibody-antigen interaction to occur, NP-40 was added to a final concentration of 1% and the lysates were cleared with Staph.A. as described below. The cleared lysates containing prebound first antibody were incubated for two hours with 20 µg/sample of goat antimouse IgG or IgM as appropriate and then treated exactly the same as immunoprecipitations from lysates.

Immunoprecipitation from Lysates

Metabolically radiolabelled lysates of SFV infected BHK cells were prepared from the homogenates described above by addition of NP-40 (Bethesda Research Laboratories, Bethesada, Md.) to 1% final concentration. The lysate was cleared by a two hour incubation with 5% (w/v) washed fixed *Staphylococcus aureus* on a microshaker at 4° C, and microfuged for 10 minutes. 50 µl aliquots of cleared lysate were incubated with either 10 µg of purified mouse monoclonal antibody or pretitrated quantities (usually between 3 and 10 µl.) of mouse or rabbit polyclonal antisera. All incubations were performed at 4° C. in an Eppendorf microshaker. After 2 hours 20 µg of a goat anti-mouse IgM or IgG second antibody, as appropriate, was added to precipitations involving mouse first antibodies. After another two hours 50 µl of a 10% (w/v) suspension of Staph.A. was added to all samples. Incubation was continued for a further two hours and the immunoprecipitates bound to the Staph.A. were washed three times in a high salt buffer at 4° C. Finally the Staph pellets were washed once in distilled water and resuspended in sample buffer containing 5 µg cold (unlabelled) SFV per sample, heated to 95° C. for 5 minutes and run unreduced on 10% SDS(sodium dodecl sulfate)-polyacrylamide gels. Gels were stained with Coomassie Blue, neutralized in PBS and incubated for 30 minutes in 0.5 M salicylate before drying and autoradiography at −70° C. using Kodak X-AR film and DuPont Cronex intensifying screens. Exposure times ranged from 12 hours to 5 days. Radioactivity in individual bands was estimated by both scanning densitometry of a range of exposures of each gel and by direct liquid scintillation counting of excised gel bands after dissolving them in 2 ml. of NEN-Solve (New England Nuclear, Inc.).

Protein Estimation

Protein was estimated by the Coomassie blue dye binding method of Bradford M., *Anal. Biochem.*, 72: 248–254 (1976) using bovine serum albumin as standard.

EXAMPLE (Anti-idiotype antibody to alphaviruses)

Production of Polyclonal Idiotype Response Against SFV E2 Cytoplasmic Domain

A synthetic peptide corresponding to the cytoplasmic tail of Semliki Forest Virus (SFV) glycoprotein E2 was produced using an Applied Biosystems automated peptide synthesizer and purified by reverse phase HPLC. The peptide synthesized had the following amino acid sequence: NH$_2$-Arg-Ser-Lys-Cys-Leu-Thr-Pro-Try-Ala-Leu-Thr-Pro-Gly-Ala-Ala-Val-Pro-Trp-Thr-Leu-Gly-Iso-Leu-Cys-Cys-Ala-Pro-Arg-Ala-His-Ala-COOH corresponding to the E2 cytoplasmic domain. This peptide was used to elicit a polyclonal immune response by both in vitro and in vivo immunization.

In vitro immunization was conducted as described herein using 10 µg of the above peptide as antigen. At the end of the five day immunization period, the supernatant containing the secreted immunoglobulin was collected, concentrated 15-fold as described previously, and found by indirect immunofluorescence to exhibit a weak virus-specific response when assayed on infected and uninfected BHK-21 cells. The non-adherent cells were then harvested and fused using polyethylene glycol with the SP-2 myeloma line. The resulting hybridomas were screened by indirect immunofluorescence on infected cells and by ELISA against the starting SFV peptide. Several positives clones were identified and one stable hybridoma cell line secreting an anti-peptide IgM was isolated, documenting the efficacy of the initial anti-peptide response.

Figure 1:
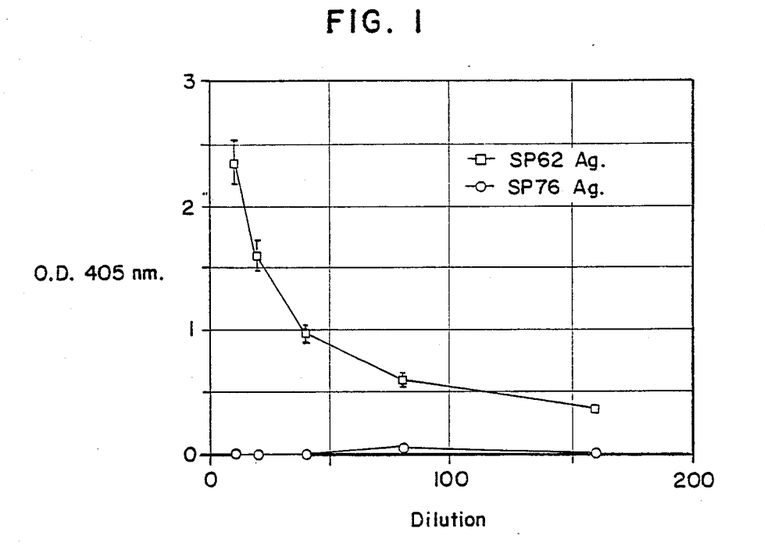
Figure 2:
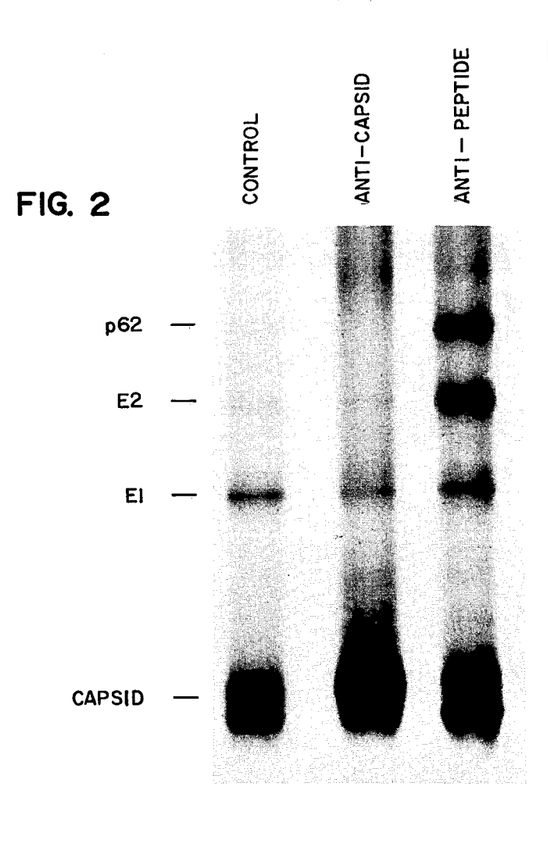
FIG. 2 shows that the polyclonal antipeptide antibody ("anti-peptide") detects the intact E2 spike glycoprotein and its uncleaved p62 precursor protein by immunoprecipitation from $^{35}$S-methionine-labelled, SFV-infected BHK-21 cells. Neither a non-immune ("control") nor an antibody to the SFV nucleocapsid ("anti-capsid") immunoprecipitated E2 or p62. Some capsid protein and a small amount of the EI spike glycoprotein are precipitated non-specifically by all antibodies.

In addition to the above in vitro immunization, conventional polyclonal anti-peptide antibodies were prepared by immunization of Balb/C mice with the unconjugated peptide. In addition to being specifically reactive against the SFV peptide (FIG. 1), these antisera also detected the intact E2 spike glycoprotein and its uncleaved p62 precursor by immunoprecipitation from $^{35}$S-methionine labelled, SFV-infected BHK-21 cells (FIG. 2). The antisera were also weakly positive by indirect immunofluorescence.

While either in vitro or in vivo procedures can be used, we have found that in vitro immunization has several significant advantages over the more conventional in vivo protocols. The antigen is delivered directly to the immune cells involved without dilution into an animal, reducing the risk of antigen sequestration or proteolysis. The response to an in vitro antigen challenge is a primary one, resulting in IgM production, and occurs before antigen-specific T suppression appears (Reading, C. L., *J. Immunol. Methods*, 53: 261-291, (1982). This implies that an antigen will elicit responses from every relevant member of the B cell repertoire, unmodulated by the tolerance effects seen in vivo. A further practical advantage is that syngeneic second round immunizations to generate anti-idiotype antibodies can be performed using the supernatant from the first in vitro immunization as antigen without further fractionation. This approach eliminates the need for identification and purification of a monospecific idiotype prior to anti-idiotype production.

Preparation of Monoclonal Anti-Idiotype Antibodies

The concentrated supernatant from the first in vitro immunization contained a polyclonal mixture of antibodies against all of the antigenic determinants present in the synthetic peptide. Following dialysis to remove any remaining peptide, this mixture of idiotypes was used without further modification as the antigen for a second round of in vitro immunization using syngeneic naive Balb/C spleen cells to produce anti-idiotype antibodies against the anti-peptide idiotypes produced during the first round of immunization.

Again, after 5 days the culture supernatant was collected, processed as above, assayed for reactivity by indirect immune fluorescence on SFV-infected cells, and stored frozen at −20° C. The stimulated nonadherent cells were harvested as before and fused with SP-2 cells to produce hybridomas secreting anti-peptide anti-idiotypic antibodies. As described below these were identified by their ability to stain permeabilized (but not non-permeabilized) SFV-infected cells, immunoprecipitate capsid protein from infected cell lysates, and specifically detect SFV-infected cells by ELISA assay.

Fusion wells containing hybridomas were first screened for virus-specific reactivity by indirect immunofluorescence on uninfected and SFV-infected BHK cells using the method described herein. Out of the 120 initial wells of the fusion, 110 contained colonies of viable hybridomas and of these, 5 exhibited virus-specific reactivity and isolated by repeated cloning as stable, IgM-secreting hybridomas.

The results described below have been obtained with one such monoclonal IgM antibody secreted by the hybridoma line designated F13.3C5. (Deposited with the American Type Culture Collection, Rockville, Md., USA and assigned accession number HB9617).

Intracellular Distribution of the F13.3C5 Antigen

Figure 3:
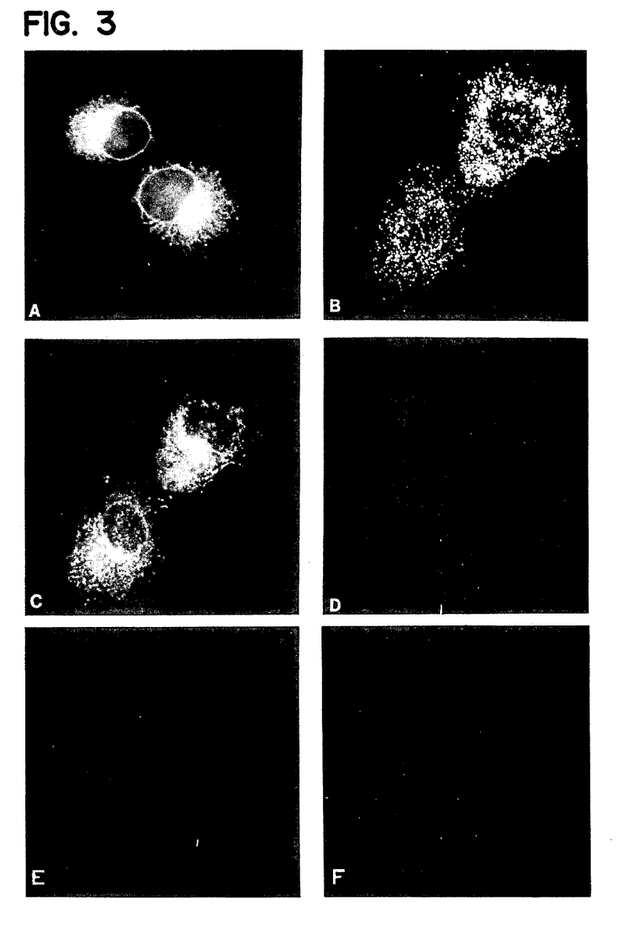

The localization of the anti-idiotype F13.3C5 antigen in SFV-infected BHK cells was first examined by indirect immunofluorescence. As shown in FIG. 3 (panels A and B), the antigen is restricted to infected cells and can only be found if the cells are permeabilized thus confirming its intracellular localization. For these experiments, BHK cells were prepared for indirect immunofluorescence by fixation in 3% (w/v) paraformaldehyde (10 min., 20° C.) with or without subsequent permeabilization with 100% methanol (as described above).

Early after infection with SFV (90 min), BHK cells expressed the F13.3C5 antigen in a fine, uniformly distributed punctate pattern throughout the cytoplasm. By 180 min, however, a second type of labelling pattern was detected being much larger, heterogenously sized, irregularly distributed and occasionally vesicular in shape. This second pattern increase at the expense of the fine punctate pattern until by 5 hr only the larger structures are labelled (FIG. 3A). The antibody did not label the nucleus, the plasma membrane, the endoplasmic reticulum or the Golgi apparatus at any time point. The pattern of labelling was also entirely distinct from that obtained with anti-spike glycoprotein antibodies (FIG. 3C and 3D). Since F13.3C5 staining was similar to that observed when infected cells were stained with polyclonal anti-capsid antibodies (FIG. 3E and 3F), it seemed likely that the anti-peptide anti-idiotype reacted with a determinant found on the SFV nucleocapsid.

Identification of the F13.3C5 Antigen as the SFV Nucleocapsid

If the E2 spike glycoprotein actually interacts specifically with a site on the viral nucleocapsid, an internal image anti-idiotype antibody, such as F13.3C5, raised against anti-E2 cytoplasmic domain immunoglobulin should specifically recognize the viral capsid protein. While the immunofluorescence results were consistent with this prediction, we next sought direct biochemical evidence for the viral antigen recognized by F13.3C5. Since the antigen was likely to be conformation-specific, we first identified conditions (see below) in which the antibody was able to recognize the cellular antigen, ELISA assays were performed using as antigen homogenates of infected cells prepared in various ways (see below). The F13.3C5 epitope was found to be extremely sensitive to detergent disruption, antibody binding being eliminated by a variety of non-ionic detergents at concentrations as low as 0.1% (e.g. Triton X-100, Triton X-114, B-D-octylglucoside, CHAPS, and Tween 20). These results are consistent with the observation that the size and hydrodynamic properties of the SFV nucleocapsid are significantly altered by such detergents. Since the F13.3C5 epitope was detectable following cell homogenization, immunoprecipitation was performed by first allowing the antibody to interact with the antigen in crude post-nuclear supernatants of $^{35}$S-methionine-labelled SFV-infected cells. The disrupted cells were then detergent-solubilized for the immunoadsorption and washing steps.

Figure 4:
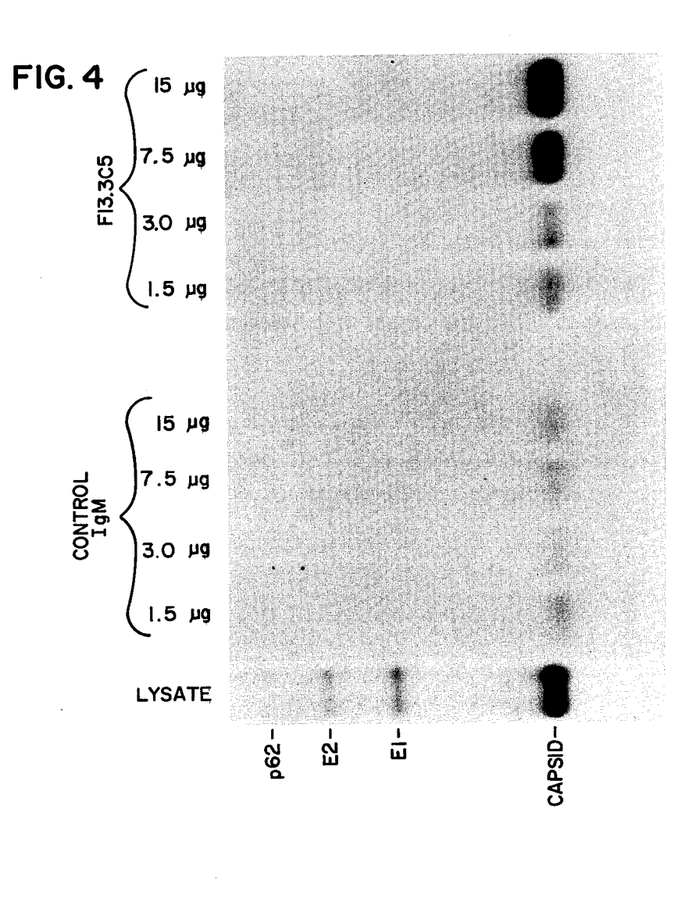
FIG. 4 shows the specific immunoprecipitation of nucleocapsids using the anti-peptide anti-idiotype F13.3C5 IgM from SFV-infected, $^{35}$S-methionine-labelled BHK-21 cells. The Figure illustrates an autoradiogram of the immunoprecipitates isolated using various concentrations (1.5 μg–15 μg) of F13.3C5 and a control (non-immune) IgM resolved by SDS-polyacrylamide gel electrophresis.
Figure 5:
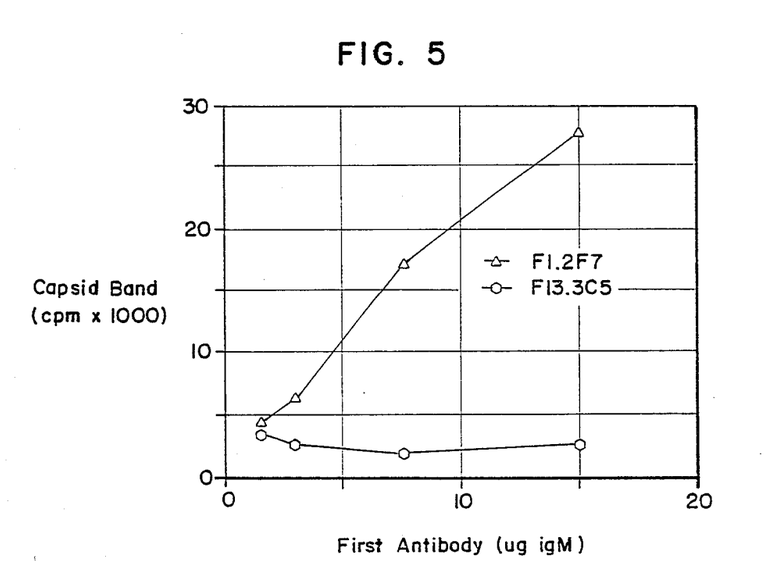

Although the SFV aapsid is particularly prone to non-specific adsorption, F13.3C5 was found to mediate the specific concentration-dependent immunoprecipitation of $^{35}$S-methionine-labelled capsid from SFV-infected cells (FIG. 4 and 5). No other viral or host cell proteins were immunoprecipitated; nor was the capsid specifically detected by an irrelevant control monoclonal IgM (FIG. 4). As a further control, F13.3C5 was also shown by ELISA not to react with the E2 cytoplasmic domain peptide (see below). by ELISA not to react with the E2 cytoplasmic domain peptide (see below).

These results confirm that the anti-idiotype antibody F13.3C5 recognizes a detergent-sensitive epitope on the SFV capsid and not a host cell neo-antigen or the starting synthetic peptide. Therefore, we believe that F13.3C5 arose as an internal image anti-idiotype antibody against the combining site of an immunoglobulin recognizing the cytoplasmic domain peptide.

However, there remains the formal if unlikely possibility that the F13.3C5 hybridoma represents the immortalization of an irrelevant B cell specificity from the naive Balb/c spleen which happens to cross react with an epitope on the SFV capsid. In order to exclude this possibility we sought to prove that F13.3C5 does indeed represent an anti-idiotype reagent by using the anti-idiotype secreting hybridoma cells as the antigen for preparation of anti-anti-idiotype monoclonals.

Preparation of Anti-Anti-Idiotype Monoclonal Antibodies by in vivo Immunization with the Anti-Idiotype Secreting Hybridoma F13.3C5

If the F13.3C5 hybridoma arose as an internal image anti-idiotype against an immunoglobulin reactive to the synthetic peptide, then it should be possible to again reconstruct the original idiotypic specificity immunologically. That is, we should be able to generate internal image anti-idiotype antibodies against F13.3C5 IgM which mimic the original idiotype and share its reactivity against the cytoplasmic domain peptide. Production of such "anti-anti-idiotype" antibodies would constitute strong evidence that F13.3C5 represents a bona fide anti-idiotype, and not an irrelevant B cell specificity which happens to cross react with an epitope on the SFV capsid. To test this prediction, we next made monoclonal antibodies against F13.3C5 IgM. An in vivo immunization protocol was used to generate antibodies of the IgG class which could be screened for binding to the IgM antigen by using isotype-specific second reagents.

Figure 6:
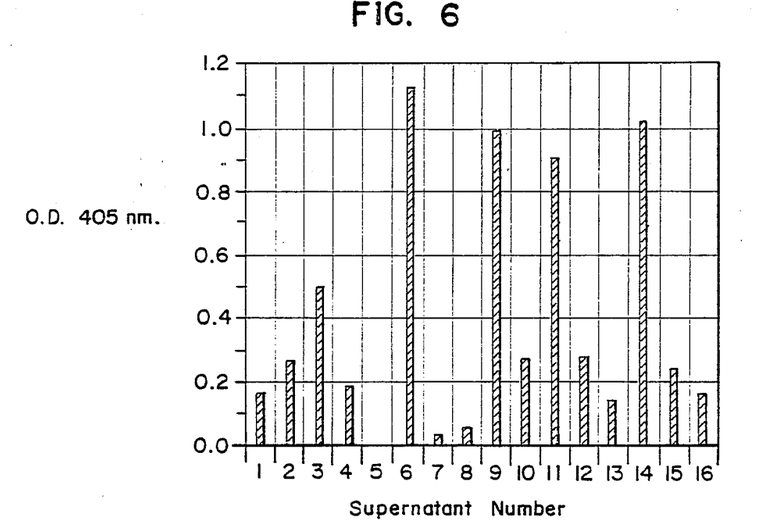
FIG. 6 shows the reactivity of murine monoclonal anti- anti-idiotypes against F13.3C5 IgM. F13.3C5 was immobilized on plastic 96 well microtiter wells (Nunc) and reactivity determined by ELISA assay..
Figure 7:
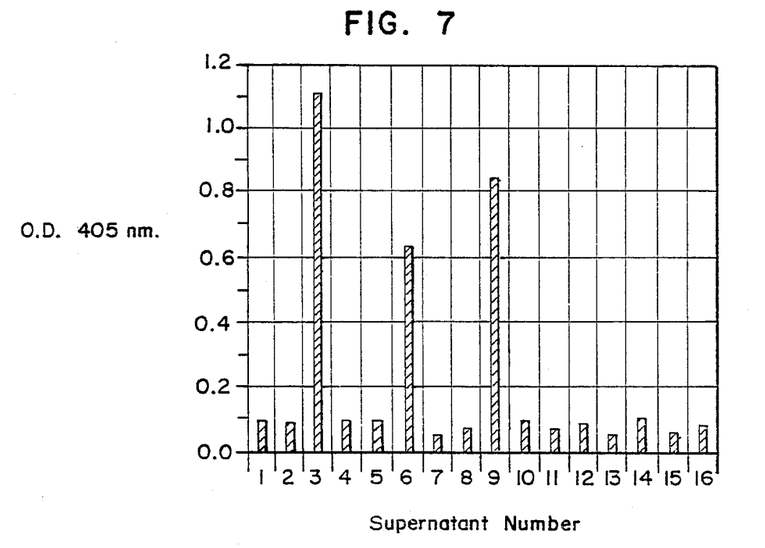
FIG. 7 shows the reactivity of murine monoclonal anti- anti-idiotypes against the starting SFV E2 synthetic peptide. Reactivity was determined by ELISA assay as in FIG. 1.

Balb/c mice were immunized and boosted once intravenously with ($2-10 \times 10^5$) washed, glutaraldehyde-fixed (1%, 10 min. at 20° C.) F13.3C5 hybridoma cells. They received a final intravenous boost of purified F13.3C5 IgM (5–50 µg) four days prior to fusion. The resulting anti-anti-idiotypic hybridoma supernatants were tested for their ability to recognize the starting E2 cytoplasmic domain peptide and the purified F13.3C5 IgM. Results obtained for the 16 highest binding supernatants to the IgM fraction are shown in FIGS. 6 and 7. Two classes of positive reactivity are clearly seen. For example, well 14 illustrates the first class: strong binding to F13.3C5 IgM (FIG. 6) but no reactivity to the starting cytoplasmic domain peptide (FIG. 7). The reactivity against F13.3C5 is specific for this IgM since no reactivity against other purified monoclonal mouse IgMs was found. This pattern of reactivity is consistent with these antibodies being "framework" anti-idiotypes (Greene, supra); i.e. antibodies which detect novel epitopes on the immunizing antibody which may be outside the antigen combining site.

In contrast, wells 3, 6, and 9 represent the second pattern of binding, with strong reactivity to both the purified F13.3C5 IgM (FIG. 6) and the cytoplasmic domain peptide (FIG. 7). For each of these isolates, the anti-peptide reactivity was specific for the cytoplasmic domain of the E2 spike glycoprotein: none were above background when assayed by ELISA on BSA or a range of other water soluble peptides of approximately similar size and composition. This pattern of reactivity is consistent with the identification of these antibodies as "internal image" anti-idiotypes.

Figure 8:
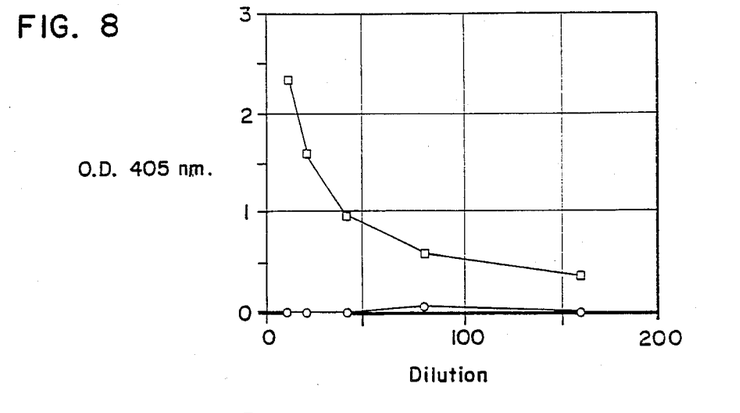
FIG. 8 shows the reactivity of a monoclonal anti-peptide IgM and an irrelevant (non-immune) IgM against the starting SFV E2 synthetic peptide. Reactivities were determined by ELISA assay. Open squares indicate reactivity of the monoclonal antipeptide antibody; closed squares indicate the reactivity of the control antibody.
Figure 9:
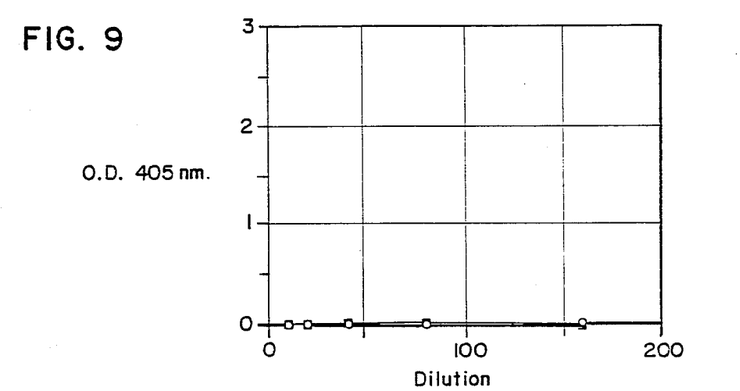
FIG. 9 shows the reactivity of the monoclonal anti-peptide anti-idiotype F13.3C5 IgM and an irrelevant (non-immune) IgM against the starting SFV E2 synthetic peptide. Reactivities were determined by ELISA assay. Open squares indicate reactivity of F13.3C5 IgM; closed squares indicate the reactivity of the control antibody. No reactivity above background was observed for either antibody.
Figure 10:
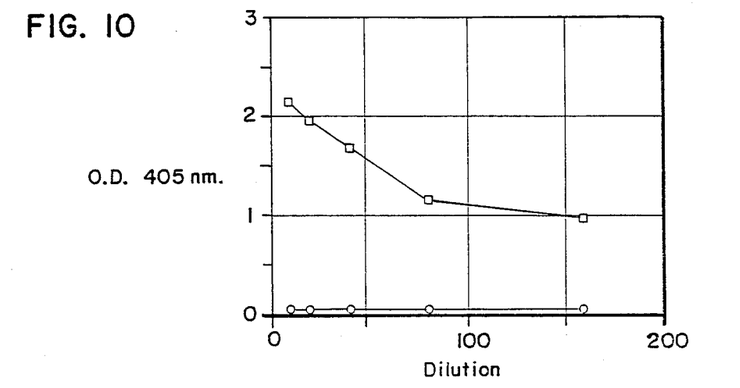
FIG. 10 shows the reactivity of the monoclonal anti- anti-idiotype 3G10D5 IgG and an irrelevant (non-immune) IgG against the starting SFV E2 synthetic peptide. Reactivities were determined by ELISA assay. Open squares indicate reactivity of 3G10.D5 IgG; closed squares indicate the reactivity of the control antibody.

A representative internal image anti-idiotype monoclonal IgG was cloned (from those hybridomas reactive against both F13.3C5 Igm and the starting SFV peptide) and designated 3G10.D5 IgG. Its reactivity for the E2 cytoplasmic domain peptide was demonstrated by the fact that its binding to the synthetic peptide was quantitatively similar to that obtained using an authentic monoclonal anti-peptide IgM (FIGS. 8 and 10). As expected, the anti-idiotype IgM with anti-capsid reactivity, F13.3C5, exhibited no binding to the starting peptide (FIG. 9).

The generation of E2 cytoplasmic domain peptide specific antibodies by immunization with the anti-idiotype F13.3C5 confirms that the capsid specificity of F13.3C5 arose as an internal image anti-idiotype raised against an anti-cytoplasmic domain immunoglobulin. This, in turn, offers formal proof at the immunological level of a specific interaction between the cytoplasmic domain of the SFV spike glycoprotein E2 and the nucleocapsid.

Conservation of the E2-Capsid Interaction

Since the specific interaction between E2 and the nuceocapsid is likely to reflect a receptor/ligand-like interaction critical to the process of virus budding, we next determined whether this determinant was conserved on the capsids of alphaviruses other than SFV. BHK-21 cells were infected with a range of related viruses and analyzed by immunofluorescence using the anti-idiotype IgM F13.3C5. Although the timecourse of appearance of the F13.3C5 antigen varied, strong labelling was observed for every alphavirus tested (Table I), the general appearance of which was similar to that observed for SFV-infected cells (FIG. 3). However, some differences in the pattern of labelled structures were also seen. For example, in cells infected with Eastern Equine Encephalitis virus, there was a tendency for the larger F13.3C5-positive structures to lie in regular arrays apparently just beneath the plasma membrane. Albeit to a lesser extent, similar patterns were also observed for the Ndumu and Venezuelan Equine Encephalitis viruses. Neither Ross River virus nor Middleburg virus caused this alignment to occur, both of which gave SFV-like patterns even in heavily infected cells at points late (>5 hr) after infection.

The extent of the conservation of the epitope recognized by F13.3C5 IgM was examined by indirect immunofluorescence experiments using BHK cells infected with viruses from the related flavivirus group. No reactivity was seen with either F13.3C5 or 3G10.D5 when assayed on BHK cells infected with a variety of flaviviruses. (Table 1).

The present invention takes advantage of the ability of the internal image class of anti-idiotype antibodies to mimic the shape of the original antigen, thereby providing an antibody useful for detecting various strains or serotypes of a group of related viruses having conserved functional domain. While the present specification describes use of an anti-idiotype antibody corresponding to the E2 spike glycoprotein to detect alphaviruses (Table I), it is to be appreciated that the principals of the present specification can be used by one of skill in the art to apply the present invention to other viruses.

It is necessary only that the amino acid sequence information be available (either deduced from nucleic acid sequence, or directly determined from protein) for the spike glycoproteins (or core proteins) of at least one member of the virus family of interest. Sequence information can be used to produce the starting synthetic peptide which is all that is required to initiate the production of anti-peptide and the subsequent anti-peptide anti-idiotype antibodies.

For example, anti-idiotype antibodies to detect the various strains of influenza virus may be provided in accordance with the present invention by employing a synthetic peptide corresponding to the cytoplasmic domains of either or both of the influenza virus spike glycoproteins hemagglutinin (HA) and neuraminidase (NA) (HA: NH2-Glu-Arg-Gly-Asn-Ile-Arg-Cys-Asn-Ile-Cys-Ile-COOH; NA: NH2-Met-Asn-Pro-Asn-Gln-Lys-COOH).

Similarly, anti-idiotype antibodies to detect human immunodeficiency virus (HIV-1) may be provided by employing a synthetic peptide corresponding to the putative cytoplasmic domain (or a portion thereof) of an HIV-1 spike glycoprotein gp4a env (in single letter code: NH2-E-R-V-I-D-V-V-Q-G-A-Y-R-A-I-R-H-I-P-R-R-I-R-Q-G-L-D-R-I-L-L-COOH).

Similarly, anti-idiotype antibodies to detect human adult T-cell leukemia virus (HTLV-I) may be provided by employing a synthetic peptide corresponding to the putative cytoplasmic domain (or a portion thereof) of an HTLV-I spike glycoprotein env (NH2-R-Q-L-R-H-L-P-S-R-V-R-Y-P-H-Y-S-L-I-K-P-D-S-S-L-COOH).

Similarly, anti-idiotype antibodies to detect an HIV-1-like simian retrovirus (SRV-1) may be provided by employing a synthetic peptide corresponding to the putative cytoplasmic domain (or a portion thereof) of an SRV-I spike glycoprotein gp20 env (in single letter code: NH2-K-L-M-T-P-I-K-H-Q-I-E-S-I-Q-A-K-P-I-Q-V-H-Y-H-R-L-E-Q-E-D-H-G-G-S-Y-L-N-L-T-COOH).

Similarly, anti-idiotype antibodies to detect retroviruses related to mouse mammary tumor virus (MMTV) may be provided by employing a synthetic peptide corresponding to the cytoplasmic domain (or a portion thereof) of the gp36 env glycoprotein (in single letter code: NH2-K-S-L-D-Q-V-Q-S-D-L-N-V-L-L-L-K-K-K-K-G-G-N-A-A-P-A-A-E-M-V-E-L-P-R-V-S-Y-T-COOH).

Similarly, anti-idiotype antibodies to detect retroviruses related to Rous sarcoma virus may be provided by employing a synthetic peptide corresponding to the cytoplasmic domain (or a portion thereof) of the gp36 env glycoprotein (in single letter code: NH2-R-K-M-I-N-S-S-I-N-Y-H-T-E-Y-R-K-M-Q-G-G-A-V-COOH).

Anti-idiotype antibodies to detect members of the rhabdovirus family may be provided by employing a synthetic peptide corresponding to the cytoplasmic domain (or a portion thereof) of the Rabies virus G protein (in single letter code: NH2-R-R-V-N-R-S-E-P-T-Q-H-N-L-R-G-T-G-R-E-V-S-V-T-P-Q-S-G-K-I-I-S-S-W-E-S-Y-K-S-G-G-E-T-L-COOH).

Anti-idiotype antibodies to detect members of the Herpes virus family may be provided by employing synthetic peptides corresponding to the cytoplasmic domains (or portions thereof) of one of the Herpes viral spike glycoproteins (e.g. gD, gE, gB, or gF).

Other anti-idiotype antibodies for detecting enveloped viruses of any class may be provided in an analogous fashion.

In each example, the anti-idiotype would be expected to recognize a highly conserved determinant specifying the interaction between external viral components (e.g. spike glycoproteins) and internal (e.g. nucleocapsid or core) viral compenents. Such specific interactions are to be expected since like the alphaviruses, all enveloped viruses escape from infected host cells by budding through host cell membranes in each a way as to include only viral components and completely or almost completely exclude host cell components. Thus, for a membrane or spike glycoprotein to be included in a nascent virion, it must specifically interact with some component of the core or nucleocapsid structure formed in the cytoplasm. It is also significant that, at least amongst the retroviruses, the greatest degree of sequence conservation in spike glycoproteins is generally found in the cytoplasmic domains.

The present invention is not to be limited in scope by the deposited hybridomas, as these are intended as specific illustrations of discrete aspects of the invention. Indeed, various modifications of the invention in addition to those shown and described herein will become apparent to those skilled in the art from the foregoing description.

TABLE 1

| Alphaviruses | F13.3C5 Reactivity | % Infected at 5 hours |
| --- | --- | --- |
| SFV | ++++ | 98 |
| Sindbis | ++++ | 95 |
| Ross River | +++ | 2 |
| Ndumu | ++++ | 10 |
| Middelburg | +++ | 3 |
| Eastern E. Encephalitis | +++++ | 100 |
| Venezuelan E.E. | +++ | 20 |
| Una | +++ | nd |
| Bebaru | +++ | nd |
| Whataroa | +++ | nd |
| O'Nyong Nyong | ++++ | nd |
| Mayaro | ++ | nd |
| Y62-33 | +++ | nd |
| Flaviviruses | | |
| Powassan | − | nd |
| Langat | − | nd |
| Karshi | − | nd |
| Kadam | − | nd |
| Tyulenyi | − | nd |

What is claimed is:

1. A method for producing an antibody directed against highly conserved domains of viral components involved in virus assembly or stabilization of internal virus structure comprising the steps of:
(a) generating a polyclonal response by in vitro immunization to an antigenic component corresponding to a viral component involved in virus assembly or stabilization of internal virus structure, said response comprising polyclonal antibodies;
(b) using said polyclonal antibodies as an antigen to produce an internal image anti-idiotype antibody by in vitro immunization, said internal image antibody recognizing and binding to a highly conserved domain of a virus which acts as binding site for said antigenic component.

2. The method of claim 1, wherein said highly conserved domain is a functional domain.

3. The method of claim 1, wherein said internal image anti-idiotype antibody recognizes a highly conserved domain of an alphavirus.

4. The method of claim 3, wherein the internal image anti-idiotype antibody is specific for the nucleocapsid of said alphaviruses.

5. The method of claim 1, wherein said polyclonal response is generated in response to a synthetic peptide corresponding to a highly conserved domain of a viral component involved in virus assembly or stabilization of internal virus structure.

6. The method of claim 5, wherein said polyclonal response is generated in response to the following synthetic peptide corresponding to the SFV E2 cytoplasmic domain: NH$_2$-Arg-Ser-Lys-Cys-Leu-Thr-Pro-Try-Ala-Leu-Thr-Pro-Gly-Ala-Ala-Val-Pro-Trp-Try-Leu-Gly-Iso-Leu-Cys-Cys-Ala-Pro-Arg-Ala-His-Ala-COOH.

7. A method for detecting the presence of an enveloped virus comprising:
(a) generating a polyclonal response by in vitro immunization to an antigenic component corresponding to a conserved cytoplasmic domain of a virus spike glycoprotein, said response comprising polyclonal antibodies;
(b) using said polyclonal antibodies as an antigen to produce an internal image anti-idiotype antibody by in vitro immunization, said internal image anti-idiotype antibody recognizing and binding to a highly conserved functional domain of a virus which acts as a binding site for said antigenic component; and
(c) detecting said virus in an immunoassay.

8. The method of claim 7, wherein said immunoassay is an indirect immunofluorescence assay.

9. The method of claim 7, wherein said immunoassay is an ELISA assay.

10. The method of claim 7, wherein said immunoassay is an immunoprecipitation assay.

11. A method for detecting presence of a virus comprising:
(a) generating a polyclonal response by in vitro immunization to an antigenic component corresponding to a highly conserved domain of a viral component involved in virus assembly or stabilization of internal virus structure, said response comprising polyclonal antibodies;
(b) using said polyclonal antibodies as an antigen to produce an internal image anti-idiotype antibody by in vitro immunization, said internal image anti-idiotype antibody recognizing and binding to a highly conserved domain of a virus which acts as a binding site for said antigenic component; and
(c) detecting said virus in an immunoassay.

12. A method for detecting the presence of an alphavirus comprising:
(a) generating a polyclonal response to a synthetic peptide corresponding to the highly conserved cytoplasmic domain of E2 glycoprotein of Semliki Forest virus in vitro, said response comprising polyclonal antibodies;
(b) using said polyclonal antibodies as an antigen to produce an internal image anti-idiotype monoclonal antibody in vitro, said internal image anti-idiotype monoclonal antibody recognizing and binding to a highly conserved functional domain of an alphavirus which acts as a binding site for the cytoplasmic domain of E2 glycoprotein; and
(c) detecting said alphavirus in an immunoassay.

13. The method of claim 12, wherein said internal image anti-idiotype antibody is generated in response to polyclonal antibodies provided in vitro against the following synthetic peptide corresponding to the SFV E2 cytoplasmic domain: NH$_2$-Arg-Ser-Lys-Cys-Leu-Thr-Pro-Try-Ala-Leu-Thr-Pro-Gly-Ala-Ala-Val-Pro-Trp-Try-Leu-Gly-Iso-Leu-Cys-Cys-Ala-Pro-Arg-Ala-His-Ala-COOH.

14. The method of claim 12, wherein said immunoassay is an immunofluorescence assay.

15. The method of claim 12, wherein said assay is an immunoprecipitation assay.

16. The method of claim 12, wherein said assay is an ELISA assay.

17. The method of claim 12, wherein said internal image anti-idiotype monoclonal antibody is IgM F13.3C5, produced by continuous cell line of ATCC Deposit No. HB9617.

18. An internal image anti-idiotype monoclonal antibody which binds to an epitope corresponding to a highly conserved functional domain of a virus nucleocapsid structure.

19. The monoclonal antibody of claim 18, wherein said virus is an alphavirus.

20. The monoclonal antibody of claim 19, wherein said antibody is anti-idiotype internal image monoclonal IgM F13.3C5 produced by continuous cell line of ATCC Deposit No. HB9617.

21. The continuous cell line of ATCC Deposit No. HB9617.

* * * * *

UNITED STATES PATENT AND TRADEMARK OFFICE
CERTIFICATE OF CORRECTION

PATENT NO. : 4,910,131

DATED : March 20, 1990

INVENTOR(S) : Ira S. Mellman et al.

It is certified that error appears in the above-identified patent and that said Letters Patent is hereby corrected as shown below:

At column 3, line 10 for "electrophresis" read --electrophoresis--.

At column 5, line 60 for "37° C.," read --37° C.--.

At column 11, line 1 for "aapsid" read --capsid--.

At column 12, line 36 for "nuceocapsid" read --nucleocapsid--.

Signed and Sealed this

Second Day of February, 1993

*Attest:*

STEPHEN G. KUNIN

*Attesting Officer*  *Acting Commissioner of Patents and Trademarks*